United States Patent [19]

Katoh et al.

[11] Patent Number: 4,769,376

[45] Date of Patent: Sep. 6, 1988

[54] CERTAIN TRI- OR TETRA-SUBSTITUTED PYRIDYL-1,2,4-TRIAZOLES USEFUL AS FUNGICIDES

[75] Inventors: Tsuguhiro Katoh, Osaka; Kiyoto Maeda; Masao Shiroshita, both of Hyogo; Norihisa Yamashita, Osaka; Yuzuru Sanemitsu, Hyogo, all of Japan; Satoru Inoue, Avon, United Kingdom

[73] Assignee: Sumitomo Chemical Company, Limited, Osaka, Japan

[21] Appl. No.: 904,061

[22] Filed: Sep. 5, 1986

[30] Foreign Application Priority Data

Sep. 5, 1985 [JP] Japan ................... 60-196157

[51] Int. Cl.⁴ .................. C07D 401/04; A01N 43/653
[52] U.S. Cl. ..................................... 514/340; 546/276
[58] Field of Search ........................ 546/276; 514/340

[56] References Cited

U.S. PATENT DOCUMENTS 4,474,599 10/1984 Rogers et al. ..................... 71/92

Primary Examiner—Alan L. Rotman
Attorney, Agent, or Firm—Sughrue, Mion, Zinn, Macpeak and Seas

[57] ABSTRACT

A novel pyridine derivative represented by the formula below, a method for preparation thereof and a plant disease protectant containing it,

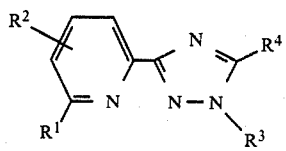

wherein $R^1$ is a $C_1$–$C_7$ alkyl group; $R^2$ is a hydrogen atom or a $C_1$–$C_2$ alkyl group, $R^3$ is a $C_1$–$C_4$ alkyl group; and $R^4$ is a $C_2$–$C_8$ alkyl group; a $C_3$–$C_7$ cycloalkyl group or a $C_4$–$C_7$ alkylcycloalkyl group, or a $C_1$–$C_3$ alkyl group substituted with a $C_3$–$C_7$ cycloalkyl group, which is effective as a plant disease protectant.

10 Claims, No Drawings

CERTAIN TRI- OR TETRA-SUBSTITUTED PYRIDYL-1,2,4-TRIAZOLES USEFUL AS FUNGICIDES

This invention relates to a pyridine derivative represented by the formula (I),

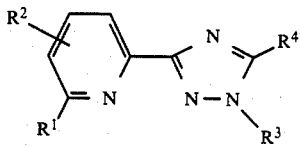

(I)

wherein $R^1$ is a $C_1$-$C_7$ alkyl group; $R^2$ is a hydrogen atom or a $C_1$-$C_2$ alkyl group; $R^3$ is a $C_1$-$C_4$ alkyl group; and $R^4$ is a $C_2$-$C_8$ alkyl group, a $C_3$-$C_7$ cycloalkyl group, a $C_4$-$C_7$ alkylcycloalkyl group or a $C_1$-$C_3$ alkyl group substituted with a $C_3$-$C_7$ cycloalkyl group, a method for preparation thereof and a plant disease protectant containing it as an active ingredient.

The inventors have made researches on compounds which have preventive and curative controlling effects against many plant diseases until the pyridine derivative represented by the formula (I) is found.

Plant diseases that can be controlled by the pyridine derivative of this invention include the followings:

Rice: *Pyricularia oryzae, Cochliobolus miyabeanus,* and *Rhizocotonia solani;*

Barley and wheat: *Erysiphe graminis* f. sp. *hordei, E. graminis* f. sp. *tritici, Gibberella zeae, Puccinia striiformis, P. graminis, P. recondita, P. hordei,* Typhula sp., *Micronectriella nivalis, Ustilago tritici, U. nuda, Pseudocercosporella herpotrichoides, Rhynchosporium secalis, Septoria tritici,* and *Leptosphaeria nodorum;*

Citrus: *Diaporthe citri, Elsinoe fawcetti, Penicillium digitatum,* and *P. italicum;*

Apple: *Sclerotinia mali, Valsa mali, Podosphaera leucotricha, Alternaria mali,* and *Venturia inaequalis;*

Pear: *Venturia nashicola, Alternaria kikuchiana,* and *Gymnosporangium haraeanum;*

Peach: *Sclerotinia cinerea, Cladosporium carpophilum,* and *Phomopsis sp;*

Grape: *Elsinoe ampelina, Glomerella cingulata, Uncinula necator,* and *Phakopsora ampelopsidis;*

Japanese persimmon: *Gloeosporium kaki, Cercospora kaki,* and *Mycosphaerella nawae;*

Melon crops: *Colletotrichum lagenarium, Sphaerotheca fuliginea,* and *Mycosphaerella melonis;*

Tomato: *Alternaria solani* and *Cladosporium fulvum;*

Eggplant: *Phomopsis vexans* and *Erysiphe cichoracearum;*

Rape: *Alternaria japonica* and *Cercosporella brassicae;*

Welsh onion: *Puccinia allii;*

Soybean: *Cercospora kikuchii, Elsinoe glycines,* and *Diaporthe phaseolorum* var. *sojae;*

Kidney bean: *Colletotrichum lindemuthianum;*

Peanut: *Mycosphaerella personatum* and *Cercospora arachidicola;*

Pea: *Erysiphe pisi;*

Potato: *Alternaria solani;*

Strawberry: *Sphaerotheca humuli;*

Tea: *Exobasidium reticulatum* and *Elsinoe leucospila;*

Tobacco: *Alternaria longipes, Erysiphe cichoracearum,* and *Colletotrichum tabacum;*

Sugar beet: *Cercospora beticola;*

Rose: *Diplocarpon rosae* and *Sphaerotheca pannosa;*

Chrysanthemum: *Septoria chrysanthemi-indici* and *Puccinia horiana;*

Crop plants: *Botrytis cinerea* and *Sclerotinia sclerotiorum.*

In the compounds of the present invention represented by the formula (I), preferred compounds are those where $R^2$ represents a hydrogen atom, $R^3$ represents a methyl group and $R^4$ represents a $C_3$-$C_6$ cycloalkyl group, an isopropyl group or a tert-butyl group.

The pyridine derivatives of this invention can be produced by reacting an amidrazone derivative of picolinic acid represented by the formula,

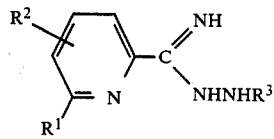

(II)

wherein $R^1$, $R^2$, and $R^3$ are defined as above, with an acid halide represented by the formula below as the first step, $$R^4COX \qquad (III)$$

wherein $R^4$ is defined as above; and X is a halogen atom, e.g. chlorine, bromine atom followed by cyclization reaction as the second step.

Generally the reaction of the first step may be carried out in the presence of a dehydrohalogenating agent in an inert solvent and the cyclization of the second step may be carried out with a base in the solvent.

Amounts of each reactant in the reactions are as follows: 1 to 2 moles for the acid halide (III), 1 to 2 moles for the dehydrohalogenating agent and 0.1 to 1 mole for the base, on the base of 1 mole of the amidrazone derivative of picolinic acid (II).

Examples of the dehydrohalogenating agent and the base used in cyclization include organic bases such as triethylamine, pyridine, and N,N-dimethylaniline, and metal alkoxides such as sodium methoxide and sodium ethoxide.

Preferred examples of the solvent used in the reaction of the first step include cyclic ethers such as dioxane and tetrahydrofuran; ketones such as acetone and methyl ethyl ketone; nitriles such as acetonitrile and isobutylonitrile; polar solvents such as pyridine, N,N-dimethylformamide, dimethylsulfoxide, and sulfolane; and mixtures thereof. These solvents may be used in combination with one of aliphatic hydrocarbons such as hexane and heptane, aromatic hydrocarbons such as benzene and toluene, halogenated hydrocarbons such as chloroform and dichloromethane, ethers such as diethyl ether, and esters such as ethyl acetate.

Preferred examples of the solvent used in the cyclization reaction of the second step are alcohols such as methanol and ethanol in addition to the above mentioned solvents.

The reaction temperature and time are generally unlimited, but the reaction of the first step may usually be carried out at −10° C. to 30° C. for 0.5 to 24 hours, and the cyclization of the second step at 20° C. to 100° C. for 0.5 to 24 hours.

After the first step of reaction is over, the reaction solution obtained therefrom is treated as in the usual manner such as concentration, and if necessary, purified by chromatography, recrystallization, or the like, before the solution is subjected to the second cyclization step.

Upon completion of the cyclization reaction, the reaction solution is concentrated and the residue is treated in the usual way e.g., dissolution in an organic solvent, washing with water, and concentration. If necessary, the obtained product may be purified by chromatography, recrystallization, or the like. Thus there is obtained the desired compound of this invention.

The following examples show the synthesis of the pyridine derivatives of this invention.

SYNTHESIS EXAMPLE 1 [SYNTHESIS OF COMPOUND (25)]

In 50 ml of tetrahydrofuran was dissolved 2 g of 6-n-butyl-N'-methyl-α-picolinic acid amidrazone, and to the solution was added 1.28 g of triethylamine. With ice cooling and stirring, 1.24 g of isobutyric acid chloride was added dropwise thereto. After stirring at room temperature for 30 minutes, 100 ml of dichloromethane was added to the solution, followed by washing with water and drying over anhydrous magnesium sulfate. The reaction product was concentrated under reduced pressure. The residue was dissolved in a solution of sodium methoxide in methanol prepared from 50 ml of methanol and 70 mg of metallic sodium. The solution was heated under refluxing for 2 hours.

After cooling to room temperature, 0.17 g of glacial acetic acid was added and the solution was concentrated under reduced pressure. The residue was dissolved in 100 ml of dichloromethane, followed by washing with water and drying over anhydrous magnesium sulfate. The solution was concentrated under reduced pressure, and the crude product was washed with hexane. Thus there was obtained 2.05 g (82% yield) of 6-n-butyl-2-(5-isopropyl-1-methyl-1,2,4-triazol-3-yl)-pyridine.

m.p. 60.3° C.

N.M.R. (CDCl$_3$) δ 0.95 ppm (t, 3H, —(CH$_2$)$_3$CH$_3$, J=6.0 Hz); 1.39, (d, 6H, —CH(CH$_3$)$_2$, J=6.3 Hz); 3.89, (s, 3H, N—CH$_3$); 7.10, (d, 1H, pyridine-H$^5$, J=7.3 Hz); 7.61, (t, 1H, pyridine-H$^4$, J=7.3 Hz); 7.93, (d, 1H, pyridine-H$^3$, J=7.3 Hz).

SYNTHESIS EXAMPLE 2 [SYNTHESIS OF COMPOUND (13)]

In 50 ml of tetrahydrofuran was dissolved 2 g of 6-ethyl-N'-methyl-α-picolinic acid amidrazone, and to the solution was added 1.36 g of triethylamine. With ice cooling and stirring, 1.81 g of cyclohexanecarbonylchloride was added dropwise thereto. After stirring at room temperature for 30 minutes, 100 ml of dichloromethane was added to the solution, followed by washing with water and drying over anhydrous magnesium sulfate. The reaction product was concentrated under reduced pressure. The residue was dissolved in a solution of sodium ethoxide in ethanol prepared from 50 ml of ethanol and 50 mg of metallic sodium. The solution was heated under refluxing for 6 hours.

After the solution was concentrated under reduced pressure. The residue was dissolved in 100 ml of chloroform, followed by washing with water and drying over anhydrous magnesium sulfate. The solution was concentrated under reduced pressure, and the crude product was washed with hexane. Thus there was obtained 2.04 g (67% yield) of 6-ethyl-2-(5-cyclohexyl-1-methyl-1,2,4-triazol-3-yl)-pyridine.

m.p. 79.2° C.

N.M.R. (CDCl$_3$) δ 1.32 ppm (t, 3H, —CH$_2$CH$_3$, J=7.8 Hz); 2.93, (q, 2H, —CH$_2$CH$_3$, J=7.8 Hz); 3.87, (s, 3H, N—CH$_3$); 7.10, (d, 1H, pyridine-H$^5$, J=7.8 Hz); 7.60, (t, 1H, pyridine-H$^4$, J=7.8 Hz); 7.89, (d, 1H, pyridine-H$^3$, J=7.8 Hz);

SYNTHESIS EXAMPLE 3 [SYNTHESIS OF COMPOUND (4)]

In 50 ml of dioxane was dissolved 2 g of 6-methyl-N'-methyl-α-picolinic acid amidrazone, and to the solution was added 1.48 g of triethylamine. With ice cooling and stirring, 1.62 g of pivaloyl chloride was added dropwise thereto. After stirring at room temperature for 30 minutes, 100 ml of dichloromethane was added to the solution, followed by washing with water and drying over anhydrous magnesium sulfate. The reaction product was concentrated under reduced pressure. The residue was dissolved in a solution of sodium methoxide in methanol prepared from 50 ml of methanol and 40 mg of metallic sodium. The solution was heated at 50° C. for 3 hours.

After that the solution was concentrated under reduced pressure. The residue was dissolved in 100 ml of ethyl acetate, followed by washing with water and drying over anhydrous magnesium sulfate. The solution was concentrated under reduced pressure, and the crude product was washed with pentane. Thus there was obtained 1.91 g (68% yield) of 6-methyl-2-(5-t-butyl-1-methyl-1,2,4-triazol-3-yl)-pyridine.

m.p. 106.5° C.

N.M.R. (CDCl$_3$) δ 1.48 ppm (s, 9H, C(CH$_3$)$_3$); 2.60, (s, 3H, —CH$_3$); 3.99, (s, 3H, N—CH$_3$); 6.99, (d, 1H, pyridine-H$^5$, J=7.8 Hz); 7.48, (t, 1H, pyridine-H$^4$, J=7.8 Hz); 7.79, (d, 1H, pyridine-H$^3$, J=7.8 Hz).

SYNTHESIS EXAMPLE 4 [SYNTHESIS OF COMPOUND (14)]

In 50 ml of tetrahydrofuran was dissolved 2 g of 6-n-propyl-N'-methyl-α-picolinic acid amidrazone, and to the solution was added 0.90 g of pyridine. With ice cooling and stirring, 1.16 g of isobutyric acid chloride was added dropwise thereto. After stirring at room temperature for 30 minutes, 100 ml of dichloromethane was added to the solution, followed by washing with water and drying over anhydrous magnesium sulfate. The reaction product was concentrated under reduced pressure. The residue was dissolved in 50 ml of ethanol and to the solution was added 0.5 g of N,N-diethylaniline. The solution was heated under refluxing for 2 hours.

After cooling to room temperature, 0.20 g of glacial acetic acid was added and the solution was concentrated under reduced pressure. The residue was dissolved in 100 ml of dichloromethane, followed by washing with water and drying over anhydrous magnesium sulfate. The solution was concentrated under reduced pressure, and the crude product was washed with hexane. Thus there was obtained 1.93 g (76% yield) of 6-n-propyl-2-(5-isopropyl-1-methyl-1,2,4-triazol-3-yl)-pyridine.

m.p. 48.6° C.

N.M.R. (CDCl$_3$) δ 0.97 ppm (t, 3H, —(CH$_2$)$_2$CH$_3$, J=6.6 Hz); 1.38, (d, 6H, —CH(CH$_3$)$_2$, J=8.4 Hz); 3.86 (s, 3H, N—CH$_3$); 7.03, (d, 1H, pyridine-H$^5$, J=7.2 Hz); 7.56, (t, 1H, pyridine-H$^4$, J=7.2 Hz); 7.85, (d, 1H, pyridine-H$^3$, J=7.2 Hz).

SYNTHESIS EXAMPLE 5 [SYNTHESIS OF COMPOUND (15)]

In 50 ml of tetrahydrofuran was dissolved 1 g of 6-n-propyl-N'-methyl-α-picolinic acid amidrazone, and to the solution was added 0.95 g of triethylamine. With ice cooling and stirring, 0.69 g of pivaloyl chloride was added dropwise thereto. After stirring at room temperature for 24 hours, the solution was concentrated under reduced pressure. The residue was dissolved in 100 ml of dichloromethane, followed by washing with water and drying over anhydrous magnesium sulfate. The solution was concentrated under reduced pressure, and the crude product was washed with hexane. Thus there was obtained 1.15 g (86% yield) of 6-n-propyl-2-(5-t-butyl-1-methyl-1,2,4-triazol-3-yl)-pyridine.

m.p 69.9° C.

N.M.R. (CDCl$_3$) δ 0.95 ppm (t, 3H, —(CH$_2$)$_2$CH$_3$, J=7.2 Hz); 1.48, (s, 9H, —C(CH$_3$)$_3$); 4.01, (s, 3H, N—CH$_3$); 7.05, (d, 1H, pyridine-H$^5$, J=7.2 Hz); 7.55, (t, 1H, pyridine-H$^4$, J=7.2 Hz); 7.85, (d, 1H, pyridine-H$^3$, J=7.2 Hz).

SYNTHESIS EXAMPLE 6 [SYNTHESIS OF COMPOUND (19)]

In 50 ml of tetrahydrofuran was dissolved 1.5 g of 6-n-propyl-N'-t-butyl-α-picolinic acid amidrazone, and to the solution was added 0.85 g of triethylamine. With ice cooling and stirring, 0.72 g of propionyl chloride was added dropwise thereto. After stirring at room temperature for 30 minutes, 100 ml of dichloromethane was added to the solution, followed by washing with water and drying over anhydrous magnesium sulfate. The reaction product was concentrated under reduced pressure. The residue was dissolved in a solution of sodium methoxide in methanol prepared from 50 ml of methanol and 70 mg of metallic sodium. The solution was heated under refluxing for 2 hours.

After that the solution was concentrated under reduced pressure. The residue was dissolved in 100 ml of dichloromethane, followed by washing with water and drying over anhydrous magnesium sulfate. The solution was concentrated under reduced pressure, and the residue was subjected to silica gel column chromatography [eluent; hexane:acetone (v/v)=3/1] to obtain 1.42 g (72% yield) of 6-n-propyl-2-(5-ethyl-1-t-butyl-1,2,4-triazol-3-yl)-pyridine.

$n_D^{25}$ 1.5343

N.M.R. (CDCl$_3$) δ 0.99 ppm (t, 3H, —CH$_2$CH$_3$, J=7.2 Hz); 1.69, (s, 9H, —C(CH$_3$)$_3$); 7.20, (d, 1H, pyridine-H$^5$, J=7.8 Hz); 7.59, (t, 1H, pyridine-H$^4$, J=7.8 Hz); 7.88, (d, 1H, pyridine-H$^3$, J=7.8 Hz).

SYNTHESIS EXAMPLE 7 [SYNTHESIS OF COMPOUND (35)]

In 50 ml of tetrahydrofuran was dissolved 2 g of 6-n-butyl-N'-methyl-α-picolinic acid amidrazone, and to the solution was added 1.36 g of triethylamine. With ice cooling and stirring, 1.81 g of cyclohexanecarbonylchloride was added dropwise thereto. After stirring at room temperature for 30 minutes, 100 ml of dichloromethane was added to the solution, followed by washing with water and drying over anhydrous magnesium sulfate. The reaction product was concentrated under reduced pressure. The residue was dissolved in a solution of sodium ethoxide in ethanol prepared from 50 ml of ethanol and 50 mg of metallic sodium. The solution was heated under refluxing for 6 hours.

After that the solution was concentrated under reduced pressure. The residue was dissolved in 100 ml of dichloromethane, followed by washing with water and drying over anhydrous magnesium sulfate. The solution was concentrated under reduced pressure, and the crude product was washed with hexane. Thus there was obtained 2.1 g (73% yield) of 6-n-butyl-2-(5-cyclohexyl-1-methyl-1,2,4-triazol-3-yl)-pyridine.

m.p 93.1° C.

N.M.R. (CDCl$_3$) δ 3.83 ppm (s, 3H, N—CH$_3$); 7.03, (d, 1H, pyridine-H$^5$, J=7.2 Hz); 7.52, (t, 1H, pyridine-H$^4$, J=7.2 Hz); 7.83, (d, 1H, pyridine-H$^3$, J=7.2 Hz).

SYNTHESIS EXAMPLE 8 [SYNTHESIS OF COMPOUND (41)]

In 50 ml of tetrahydrofuran was dissolved 2 g of 6-n-butyl-5-methyl-N'-methyl-α-picolinic acid amidrazone, and to the solution was added 1.28 g of triethylamine. With ice cooling and stirring, 1.24 g of isobutyric acid chloride was added dropwise thereto. After stirring at room temperature for 30 minutes, 100 ml of dichloromethane was added to the solution, followed by washing with water and drying over anhydrous magnesium sulfate. The reaction product was concentrated under reduced pressure. The residue was dissolved in a solution of sodium methoxide in methanol prepared from 50 ml of methanol and 70 mg of metallic sodium. The solution was heated under refluxing for 2 hours.

After cooling to room temperature, 0.17 g of glacial acetic acid was added and the solution was concentrated under reduced pressure. The residue was dissolved in 100 ml of dichloromethane, followed by washing with water and drying over anhydrous magnesium sulfate. The solution was concentrated under reduced pressure, and the crude product was washed with hexane. Thus there was obtained 2.0 g (81% yield) of 6-n-butyl-2-(5-isopropyl-1-methyl-1,2,4-triazol-3-yl)pyridine.

m.p. 58.1° C.

N.M.R. (CDCl$_3$) δ 1.39 ppm (d, 6H, —CH(CH$_3$)$_2$, J=6.6 Hz); 2.35, (s, 3H, —CH$_3$); 3.93, (s, 3H, N—CH$_3$); 7.45, (d, 1H, pyridine-H$^4$, J=8.4 Hz); 7.85, (d, 1H, pyridine-H$^3$, J=8.4 Hz).

SYNTHESIS EXAMPLE 9 [SYNTHESIS OF COMPOUND (46)]

In 50 ml of tetrahydrofuran was dissolved 1.5 g of 6-isobutyl-N'-methyl-α-picolinic acid amidrazone, and to the solution was added 1.11 g of triethylamine. With ice cooling and stirring, 0.93 g of isobutyric acid chloride was added dropwise thereto. After stirring at room temperature for 30 minutes, 100 ml of dichloromethane was added to the solution, followed by washing with water and drying over anhydrous magnesium sulfate. The reaction product was concentrated under reduced pressure. The residue was dissolved in a solution of sodium methoxide in methanol prepared from 50 ml of methanol and 70 mg of metallic sodium. The solution was heated under refluxing for 2 hours.

After cooling to room temperature, 0.17 g of glacial acetic acid was added and the solution was concentrated under reduced pressure. The residue was dissolved in 100 ml of dichloromethane, followed by washing with water and drying over anhydrous magnesium sulfate. The solution was concentrated under reduced pressure, and the crude product was washed with hexane. Thus there was obtained 1.41 g (75% yield) of 6-isobutyl-2-(5-isopropyl-1-methyl-1,2,4-triazol-3-yl)-pyridine.

m.p. 80.1° C.

N.M.R. (CDCl₃) δ 0.93 ppm (d, 6H, —CH₂CH(CH₃)₂, J=6.0 Hz); 1.50, (d, 6H, —CH(CH₃)₂, J=6.6 Hz); 3.90, (s, 3H, N—CH₃); 7.10 d, 1H, pyridine-H⁵, J=7.2 Hz); 7.63, (t, 1H, pyridine-H⁴, J=7.2 Hz); 7.95, (d, 1H, pyridine-H³, J=7.2 Hz).

SYNTHESIS EXAMPLE 10 [SYNTHESIS OF COMPOUND (51)]

In 50 ml of tetrahydrofuran was dissolved 1.5 g of 6-n-amyl-N'-methyl-α-picolinic acid amidrazone, and to the solution was added 1.28 g of triethylamine. With ice cooling and stirring, 1.24 g of isobutyric acid chloride was added dropwise thereto. After stirring at room temperature for 30 minutes, 100 ml of dichloromethane was added to the solution, followed by washing with water and drying over anhydrous magnesium sulfate. The reaction product was concentrated under reduced pressure. The residue was dissolved in a solution of sodium methoxide in methanol prepared from 50 ml of methanol and 70 mg of metallic sodium. The solution was heated under refluxing for 2 hours.

After cooling to room temperature, 0.17 g of glacial acetic acid was added and the solution was concentrated under reduced pressure. The residue was dissolved in 100 ml of dichloromethane, followed by washing with water and drying over anhydrous magnesium sulfate. The solution was concentrated under reduced pressure, and the residue was subjected to silica gel column chromatography [eluent; hexane:acetone (v/v)=3/1] to obtain 1.49 g (81% yield) of 6-n-amyl-2-(5-isopropyl-1-methyl-1,2,4-triazol-3-yl)-pyridine.

$n_D^{22}$ 1.5371

N.M.R. (CDCl₃) δ 1.38 ppm (d, 6H, —CH(CH₃)₂, J=6.6 Hz); 3.87, (s, 3H, N—CH₃); 7.11, (d, 1H, pyridine-H⁵, J=7.2 Hz); 7.62; (t, 1H, pyridine-H⁴, J=7.2 Hz); 7.93, (d, 1H, pyridine-H³, J=7.2 Hz).

Table 1 shows some examples of the pyridine derivatives of this invention that can be produced according to the above-mentioned method.

TABLE 1

Pyridine derivatives represented by the formula:

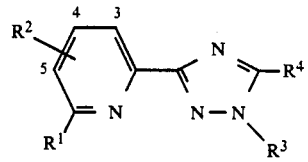

| Compound of this invention | R¹ | R² | R³ | R⁴ | Physical constant |
|---|---|---|---|---|---|
| (1) | CH₃ | H | CH₃ | C₂H₅ | m.p. 71.1° C. |
| (2) | CH₃ | H | CH₃ | n-C₃H₇ | m.p. 59.1° C. |
| (3) | CH₃ | H | CH₃ | i-C₃H₇ | $n_D^{25}$ 1.5499 |
| (4) | CH₃ | H | CH₃ | t-C₄H₉ | m.p. 106.5° C. |
| (5) | CH₃ | H | CH₃ | i-C₄H₉ | $n_D^{25}$ 1.5447 |
| (6) | CH₃ | H | CH₃ | CH₂C(CH₃)₃ | m.p. 88.2° C. |
| (7) | CH₃ | H | CH₃ | cyclopropyl | m.p. 65.7° C. |
| (8) | CH₃ | H | CH₃ | cyclobutyl | m.p. 80.4° C. |
| (9) | CH₃ | H | CH₃ | cyclohexyl | $n_D^{25}$ 1.5525 |
| (10) | C₂H₅ | H | CH₃ | i-C₃H₇ | $n_D^{25}$ 1.5431 |
| (11) | C₂H₅ | H | CH₃ | t-C₄H₉ | $n_D^{25}$ 1.5430 |
| (12) | C₂H₅ | H | CH₃ | cyclopropyl | m.p. 65.2° C. |
| (13) | C₂H₅ | H | CH₃ | cyclohexyl | m.p. 79.2° C. |
| (14) | n-C₃H₇ | H | CH₃ | i-C₃H₇ | m.p. 48.6° C. |
| (15) | n-C₃H₇ | H | CH₃ | t-C₄H₉ | m.p. 69.9° C. |

TABLE 1-continued
Pyridine derivatives represented by the formula:

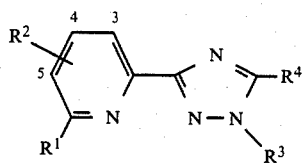

| Compound of this invention | R¹ | R² | R³ | R⁴ | Physical constant |
|---|---|---|---|---|---|
| (16) | n-C$_3$H$_7$ | H | CH$_3$ | C(CH$_3$)(CH$_3$)CH$_2$CH$_3$ | m.p. 67.0° C. |
| (17) | n-C$_3$H$_7$ | H | CH$_3$ | cyclopropyl | m.p. 74.1° C. |
| (18) | n-C$_3$H$_7$ | H | CH$_3$ | cyclohexyl | m.p. 94.1° C. |
| (19) | n-C$_3$H$_7$ | H | t-C$_4$H$_9$ | C$_2$H$_5$ | $n_D^{25}$ 1.5343 |
| (20) | n-C$_3$H$_7$ | H | t-C$_4$H$_9$ | n-C$_3$H$_7$ | $n_D^{25}$ 1.5299 |
| (21) | i-C$_3$H$_7$ | H | CH$_3$ | i-C$_3$H$_7$ | $n_D^{25}$ 1.5453 |
| (22) | i-C$_3$H$_7$ | H | CH$_3$ | t-C$_4$H$_9$ | m.p. 95.5° C. |
| (23) | n-C$_4$H$_9$ | H | CH$_3$ | C$_2$H$_5$ | $n_D^{26}$ 1.5359 |
| (24) | n-C$_4$H$_9$ | H | CH$_3$ | n-C$_3$H$_7$ | $n_D^{26}$ 1.5343 |
| (25) | n-C$_4$H$_9$ | H | CH$_3$ | i-C$_3$H$_7$ | m.p. 60.3° C. |
| (26) | n-C$_4$H$_9$ | H | CH$_3$ | i-C$_4$H$_9$ | $n_D^{26}$ 1.5322 |
| (27) | n-C$_4$H$_9$ | H | CH$_3$ | sec-C$_4$H$_9$ | $n_D^{25}$ 1.5341 |
| (28) | n-C$_4$H$_9$ | H | CH$_3$ | CH(C$_2$H$_5$)$_2$ | $n_D^{26}$ 1.5294 |
| (29) | n-C$_4$H$_9$ | H | CH$_3$ | CH(CH$_3$)CH$_2$CH$_2$CH$_3$ | $n_D^{25}$ 1.5313 |
| (30) | n-C$_4$H$_9$ | H | CH$_3$ | n-C$_6$H$_{13}$ | m.p. 40.2° C. |
| (31) | n-C$_4$H$_9$ | H | CH$_3$ | n-C$_7$H$_{15}$ | m.p. 35.4° C. |
| (32) | n-C$_4$H$_9$ | H | CH$_3$ | cyclopropyl | $n_D^{25}$ 1.5540 |
| (33) | n-C$_4$H$_9$ | H | CH$_3$ | cyclobutyl | $n_D^{26}$ 1.5550 |
| (34) | n-C$_4$H$_9$ | H | CH$_3$ | cyclopentyl | $n_D^{26}$ 1.5490 |
| (35) | n-C$_4$H$_9$ | H | CH$_3$ | cyclohexyl | m.p. 93.1° C. |
| (36) | n-C$_4$H$_9$ | H | CH$_3$ | —CH$_2$—cyclohexyl | $n_D^{26}$ 1.5420 |

TABLE 1-continued

Pyridine derivatives represented by the formula:

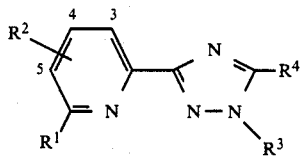

| Compound of this invention | R¹ | R² | R³ | R⁴ | Physical constant |
|---|---|---|---|---|---|
| (37) | n-$C_4H_9$ | H | $CH_3$ | —$(CH_2)_2$—⟨H⟩ | m.p. 67.8° C. |
| (38) | n-$C_4H_9$ | H | $CH_3$ | —$(CH_2)_3$—⟨H⟩ | m.p. 42.4° C. |
| (39) | n-$C_4H_9$ | H | $CH_3$ | —C(CH₃)(CH₂–CH₂) (cyclopropyl with CH₃) | $n_D^{25}$ 1.5442 |
| (40) | n-$C_4H_9$ | 4-$CH_3$ | $CH_3$ | i-$C_3H_7$ | $n_D^{22}$ 1.5335 |
| (41) | n-$C_4H_9$ | 5-$CH_3$ | $CH_3$ | i-$C_3H_7$ | m.p. 58.1° C. |
| (42) | n-$C_4H_9$ | 5-$CH_3$ | $CH_3$ | t-$C_4H_9$ | m.p. 112.7° C. |
| (43) | n-$C_4H_9$ | 5-$C_2H_5$ | $CH_3$ | i-$C_3H_7$ | $n_D^{24}$ 1.5350 |
| (44) | n-$C_4H_9$ | 5-$C_2H_5$ | $CH_3$ | t-$C_4H_9$ | m.p. 81.5° C. |
| (45) | n-$C_4H_9$ | 5-$C_2H_5$ | $CH_3$ | ⟨H⟩ | m.p. 71.4° C. |
| (46) | i-$C_4H_9$ | H | $CH_3$ | i-$C_3H_7$ | m.p. 80.1° C. |
| (47) | i-$C_4H_9$ | H | $CH_3$ | ⟨H⟩ | m.p. 77.8° C. |
| (48) | sec-$C_4H_9$ | H | $CH_3$ | i-$C_3H_7$ | m.p. 95.5° C. |
| (49) | sec-$C_4H_9$ | H | $CH_3$ | t-$C_4H_9$ | m.p. 52.1° C. |
| (50) | sec-$C_4H_9$ | H | $CH_3$ | ⟨H⟩ | m.p. 98.5° C. |
| (51) | n-$C_5H_{11}$ | H | $CH_3$ | i-$C_3H_7$ | $n_D^{22}$ 1.5371 |
| (52) | n-$C_5H_{11}$ | H | $CH_3$ | ⟨H⟩ | m.p. 93.6° C. |

The amidrozone derivative of picolinic acid represented by the formula (II), which is the starting material for producing the pyridine derivatives of this invention, can be prepared in the following scheme.

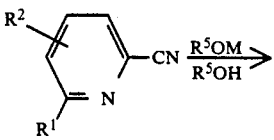

(V)    (M = alkali metal)

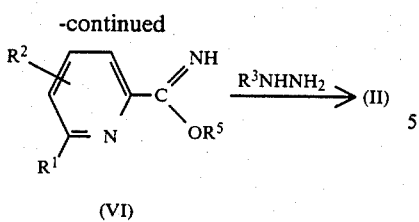

A picolinecarbonitrile derivative represented by the formula (V) below is prepared according to the method described in J. Org. Chem., 48, 1375-1377 (1983).

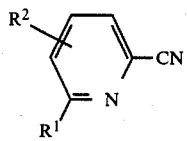

where $R^1$ and $R^2$ are defined as above. This derivative is reacted with 0.1 to 1 mole of a lower alkali metal alkoxide, for 1 mole of the picolinecarbonitrile derivative, in a lower alcohol, preferably methanol or ethanol, at 10° C. to 50° C. for 1 to 48 hours. The reaction solution is neutralized with an acid, e.g., acetic acid, followed by concentration. The residue is dissolved in a solvent e.g., diethyl ether, and insoluble alkali metal salts are filtered off. The filtrate is concentrated to give an imidate represented by the formula (VI) below.

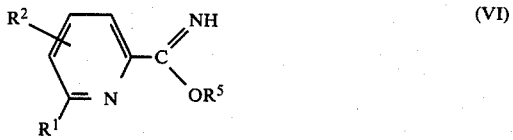

where $R^1$ and $R^2$ are defined as above; and $R^5$ is a lower alkyl group.

The imidate (VI) is then reacted with 1 to 1.5 moles of a hydrazine derivative represented by the formula (VII) below for 1 mole of the imidate:

where $R^3$ is defined as above, at 10° C. to 30° C. for 5 to 120 hours in a lower alcohol, e.g., methanol and ethanol or an ether, e.g., diethyl ether and tetrahydrofuran.

Upon completion of the reaction, the reaction solution, with an acid, e.g., acetic acid added, is concentrated, and the residue is dissolved in an organic solvent, e.g., ether, and insoluble materials are filtered off. The filtrate is treated in the usual way such as concentration under reduced pressure. If necessary, the product may be purified by chromatography or the like. Thus there is obtained the desired amidrazone derivative of picolinic acid (II).

In the meantime, the amidrazone derivative of picolinic acid (II) can be prepared by reacting the picolinecarbonitrile derivative (V) with 1 to 1.5 moles of hydrazine derivative (VII) at 10° C. to 30° C. for 10 to 48 hours in a solvent such as lower alcohol, e.g., methanol and ethanol, and ether, e.g., diethyl ether and tetrahydrofuran. However, this method is not preferable because of low yields and long reaction periods. So the synthetic method through the imidate (VI) is preferable.

The following reference examples show the preparation of the amidrazone derivative of picolinic acid.

REFERENTIAL EXAMPLES

Preparation of 6-methyl-N'-methyl-picolinic acid amidrazone 10 g of 2-cyano-6-methylpyridine was dissolved in a solution of sodium methoxide in methanol prepared from 100 ml of methanol and 0.39 g of metallic sodium. After standing overnight, 1 g of acetic acid was added thereto, followed by concentration under reduced pressure. The resulting residue was dissolved in 200 ml of ether and insoluble materials were filtered out. The filtrate was concentrated under reduced pressure. The concentrate was dissolved in 100 ml of methanol, followed by adding 4.3 g of methylhydrazine and allowed to stand overnight. The reaction solution was concentrated under reduced pressure to give 10.8 g (yield 78%) of 6-methyl-N'-methyl-picolinic acid amidrazone. $n_D^{27}$ 1.5937

Table 2 shows some examples of amidrazone derivative of picolinic acid (II) that can be prepared by the above-mentioned method.

TABLE 2

Amidrazone derivative of picolinic acid

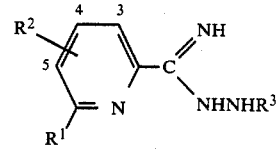

| Compound | $R^1$ | $R^2$ | $R^3$ | Physical constant |
|---|---|---|---|---|
| a | $C_2H_5$ | H | $CH_3$ | $n_D^{27}$ 1.5821 |
| b | $n\text{-}C_5H_{11}$ | H | $CH_3$ | $n_D^{27}$ 1.5459 |
| c | $i\text{-}C_4H_9$ | H | $CH_3$ | $n_D^{27}$ 1.5553 |
| d | $sec\text{-}C_4H_9$ | H | $CH_3$ | $n_D^{27}$ 1.5614 |
| e | $n\text{-}C_4H_9$ | $5\text{-}C_2H_5$ | $CH_3$ | $n_D^{27}$ 1.5481 |

The pyridine derivatives of this invention may be used as such as an active ingredient of a plant disease protectant; however, it is usually mixed with a solid carrier, liquid carrier, surface active agent, and other adjuvants and formulated into an emulsion, wettable powder, suspension, granule, dust, or liquid.

These formulations may contain 0.1 to 99 wt%, preferably 0.2 to 95 wt%, of the compound of this invention as an active ingredient.

Examples of solid carriers include kaolin clay, attapulgite clay, bentonite, Japanese acid clay, pyrophyllite, talc, diatomaceous earth, calcite, corncob powder, walnut shell powder, urea, ammonium sulfate, and synthetic hydrated silica, which are in the form of finely divided powder or granule. Examples of liquid carrier include aromatic hydrocarbons, e.g., xylene and methylnaphthalene; alcohols, e.g., isopropanol, ethylene glycol, and cellosolve; ketone, e.g., acetone, cyclohexanone, and isophorone; vegetable oils e.g., soybean oil and cottonseed oil; dimethylsufoxide, acetonitrile, and water.

Examples of surface active agents for emulsification, dispersion, and wetting include anionic surface active agents such as alkyl sulfate salt, alkyl or aryl sulfonate, dialkylsulfosuccinate, polyoxyethylene alkylarylether phosphate salt, and naphthalene sulfonic acid-formalin condensate; and nonionic surface active agents such as polyoxyethylene alkyl ether, polyoxyethylene-polyoxypropylene block copolymer, sorbitan-fatty acid ester, and polyoxyethylene-sorbitan fatty acid ester. Examples of adjuvants include ligninsulfonate, alginate, polyvinyl alcohol, gum arabic, CMC (carboxymethylcellulose), and PAP (isopropyl acidphosphate).

The following examples illustrate the formulations containing the pyridine derivatives of this invention. The quantities are expressed in parts by weight.

FORMULATION EXAMPLE 1

A wettable powder was prepared by mixing and pulverizing 50 parts of each of the compounds (1)–(52), 3 parts of calcium ligninsulfonate, 2 parts of sodium lauryl sulfate, and 45 parts of synthetic hydrated silica.

FORMULATION EXAMPLE 2

An emulsifiable concentrate was prepared by thoroughly mixing 10 parts of each of the compounds (1)–(52), 14 parts of polyoxyethylene styrylphenyl ether, 6 parts of calcium dodecylbenzenesulfonate, and 70 parts of xylene.

FORMULATION EXAMPLE 3

A granule was prepared by mixing and pulverizing 2 parts of each of the compounds (1)–(52), 1 part of synthetic hydrated silica, 2 parts of calcium ligninsulfonate, 30 parts of bentonite, and 65 parts of kaolin clay, followed by kneading with water, granulation, and drying.

FORMULATION EXAMPLE 4

A suspension was prepared by mixing 25 parts of each of the compounds (1)–(52), 3 parts of polyoxyethylene sorbitanmonooleate, 3 parts of CMC, and 69 parts of water, followed by wet grinding to give a particle size smaller than 5 microns.

FORMULATION EXAMPLE 5

A dust was prepared by mixing and pulverizing 2 parts of each of the compounds (1)–(52), 88 parts of kaolin clay, and 10 parts of talc.

FORMULATION EXAMPLE 6

A liquid formulation was prepared by mixing 10 parts of each of the compounds (1)–(52), 1 part of polyoxyethylene styrylphenyl ether, and 89 parts of water.

These formulations are used as such or after dilution with water for foliage application or soil treatment or soil incorporation. They may also be used in combination with other plant disease protectants for their enhanced control effect. Further, they may be used in combination with an insecticide, acaricide, nematicide, herbicide, plant growth regulator, fertilizer, and soil conditioner.

In the case where the compound of this invention is used as an active ingredient of a plant disease protectant, the dosage varies depending on the weather conditions, formulation, application time, application method, application place, object diseases, and object crops. The dosage is usually 0.5 to 50 g for an area of 1 are. In the case of emulsion, wettable powder, suspension, or liquid formulation which is diluted with water prior to application, the concentration should be 0.005 to 0.5%. Granules and dusts are used as such without dilution.

The following test examples demonstrate the effectiveness of the pyridine derivatives of this invention used as an active ingredient of plant disease protectants.

The pyridine derivatives of this invention used in the test examples are identified by the compound numbers shown in Table 1, and the compounds used for control are identified by the compound symbols shown in Table 3.

TABLE 3

| Compound symbol | Compound | Remarks |
|---|---|---|
| A | i-C$_3$H$_7$O\P(=O)—SCH$_2$—C$_6$H$_5$ / i-C$_3$H$_7$O | Commercial fungicide IBP |
| B | Validamycin A | Commercial fungicide |
| C | benzimidazole—NHCOCH$_3$ | Commercial fungicide MBC |
| D | cyclohexene-dicarboximide-N—S—CCl$_2$—CHCl$_2$ | Commercial fungicide Captafol |
| E | benzimidazole—NHCOOCH$_3$, N-CONHC$_4$H$_9$—n | Commercial fungicide Benomyl |

The controlling effect was evaluated by visually observing the degree of fungus colony and infected area of on the leaves and stems of the test plants. The results of evaluation were expressed in terms of six ratings as follows:

"5": Not observed at all.
"4": Observed on about 10% of the leaves and stems.
"3": Observed on about 30% of the leaves and stems.
"2": Observed on about 50% of the leaves and stems.
"1": Observed on about 70% of the leaves and stems.
"0": Same as control.

Test Example 1

Test for preventive controlling effect on blast (*Pyricularia oryzae*) of rice

Rice seeds (var.: Kinki No. 33) were sown in the sandy loam filled in a plastic pot. After raising for 20 days in a greenhouse, the seedlings were subjected to foliage application with a spray liquid of the emulsion prepared according to Formulation Example 2. After application, the seedlings were air-dried and then inoculated with spores of *Pyricularia oryzae* by spraying a suspension of spores. The inoculated seedlings were grown in a dark damp place at 28° C. for 4 days, and the controlling effect was examined. The results are shown in Table 4.

TABLE 4

| Compound No. | Concentration of active ingredient (ppm) | Control effect |
|---|---|---|
| present compound | | |
| (1) | 200 | 5 |
| (2) | 200 | 5 |
| (3) | 200 | 5 |

TABLE 4-continued

| Compound No. | Concentration of active ingredient (ppm) | Control effect |
|---|---|---|
| (4) | 200 | 5 |
| (5) | 200 | 5 |
| (6) | 200 | 5 |
| (8) | 200 | 5 |
| (9) | 200 | 5 |
| (10) | 200 | 5 |
| (11) | 200 | 5 |
| (12) | 200 | 5 |
| (13) | 200 | 5 |
| (14) | 200 | 5 |
| (15) | 200 | 5 |
| (16) | 200 | 5 |
| (17) | 200 | 5 |
| (18) | 200 | 5 |
| (19) | 200 | 5 |
| (20) | 200 | 5 |
| (21) | 200 | 5 |
| (22) | 200 | 5 |
| (23) | 200 | 5 |
| (24) | 200 | 5 |
| (25) | 200 | 5 |
| (26) | 200 | 5 |
| (27) | 200 | 5 |
| (28) | 200 | 5 |
| (29) | 200 | 5 |
| (30) | 200 | 5 |
| (31) | 200 | 5 |
| (32) | 200 | 5 |
| (33) | 200 | 5 |
| (34) | 200 | 5 |
| (35) | 200 | 5 |
| (36) | 200 | 5 |
| (37) | 200 | 5 |
| (38) | 200 | 5 |
| (39) | 200 | 5 |
| (40) | 200 | 5 |
| (41) | 200 | 5 |
| (42) | 200 | 5 |
| (43) | 200 | 5 |
| (44) | 200 | 5 |
| (45) | 200 | 5 |
| (46) | 200 | 5 |
| (47) | 200 | 5 |
| (48) | 200 | 5 |
| (49) | 200 | 5 |
| (50) | 200 | 5 |
| (51) | 200 | 5 |
| (52) | 200 | 5 |
| reference compound | | |
| A | 200 | 4 |

TEST EXAMPLE 2

Test for curative controlling effect on blast (*Pyricularia oryzae*) of rice

Rice seeds (var.: Kinki No. 33) were sown in the sandy loam filled in a plastic pot. After raising for 20 days in a greenhouse, the seedlings were inoculated with spores of *Pyricularia oryzae* by spraying a suspension of spores. The inoculated seedlings were grown in a dark damp place at 28° C. for 16 hours. The seedlings were subjected to foliage application with a spray liquid of the wettable powder prepared according to Formulation Example 1. After application, the seedlings were grown in a dark damp place at 28° C. for 3 days, and the controlling effect was examined. The results are shown in Table 5.

TABLE 5

| Compound No. | Concentration of active ingredient (ppm) | Control effect |
|---|---|---|
| present compound | | |
| (4) | 200 | 5 |
| (8) | 200 | 5 |
| (9) | 200 | 5 |
| (10) | 200 | 5 |
| (11) | 200 | 5 |
| (12) | 200 | 5 |
| (13) | 200 | 5 |
| (14) | 200 | 5 |
| (15) | 200 | 5 |
| (16) | 200 | 5 |
| (17) | 200 | 5 |
| (18) | 200 | 5 |
| (19) | 200 | 5 |
| (21) | 200 | 5 |
| (22) | 200 | 5 |
| (23) | 200 | 5 |
| (24) | 200 | 5 |
| (25) | 200 | 5 |
| (26) | 200 | 5 |
| (27) | 200 | 5 |
| (28) | 200 | 5 |
| (29) | 200 | 5 |
| (30) | 200 | 5 |
| (31) | 200 | 5 |
| (32) | 200 | 5 |
| (33) | 200 | 5 |
| (34) | 200 | 5 |
| (37) | 200 | 5 |
| (39) | 200 | 5 |
| (40) | 200 | 5 |
| (41) | 200 | 5 |
| (42) | 200 | 5 |
| (43) | 200 | 5 |
| (46) | 200 | 5 |
| (47) | 200 | 5 |
| (48) | 200 | 5 |
| (49) | 200 | 5 |
| (50) | 200 | 5 |
| (51) | 200 | 5 |
| (52) | 200 | 5 |
| reference compound | | |
| A | 200 | 4 |

TEST EXAMPLE 3

Test for preventive controlling effect on sheath blight (*Rhizoctonia solani*) of rice Rice seeds (var.: Kinki No. 33) were sown in the sandy loam filled in a plastic pot. After raising for 28 days in a greenhouse, the seedlings were subjected to foliage application with a spray liquid of the suspension prepared according to Formulation Example 4. After application, the seedlings were air-dried and then inoculated with mycelia of *Rhizoctonia solani* by spraying an agar suspension containing the fungi. The inoculated seedlings were grown in a dark damp place at 28° C. for 4 days, and the controlling effect was examined. The results are shown in Table 6.

TABLE 6

| Compound No. | Concentration of active ingredient (ppm) | Control effect |
|---|---|---|
| present compound | | |
| (2) | 500 | 5 |
| (6) | 500 | 5 |
| (8) | 500 | 5 |
| (9) | 500 | 5 |
| (11) | 500 | 5 |
| (13) | 500 | 5 |
| (14) | 500 | 5 |
| (15) | 500 | 5 |
| (16) | 500 | 5 |
| (18) | 500 | 5 |
| (20) | 500 | 5 |

TABLE 6-continued

| Compound No. | Concentration of active ingredient (ppm) | Control effect |
|---|---|---|
| (21) | 500 | 5 |
| (22) | 500 | 5 |
| (23) | 500 | 5 |
| (25) | 500 | 5 |
| (26) | 500 | 5 |
| (29) | 200 | 5 |
| (30) | 200 | 5 |
| (32) | 200 | 5 |
| (33) | 200 | 5 |
| (34) | 200 | 5 |
| (35) | 200 | 5 |
| (36) | 200 | 5 |
| (37) | 200 | 5 |
| (38) | 200 | 5 |
| (39) | 200 | 5 |
| (40) | 200 | 5 |
| (41) | 200 | 5 |
| (42) | 200 | 5 |
| (43) | 200 | 5 |
| (44) | 200 | 5 |
| (45) | 200 | 5 |
| (46) | 200 | 5 |
| (47) | 200 | 5 |
| (48) | 200 | 5 |
| (49) | 200 | 5 |
| (50) | 200 | 5 |
| (51) | 200 | 5 |
| reference compound | | |
| B | 60 | 4 |

TEST EXAMPLE 4

Test for preventing controlling effect on eyespot (*Pseudocercosporella herpotrichloides*) of wheat Wheat seeds (var.: Norin No. 73) were sown in the sandy loam filled in a plastic pot. After raising for 10 days in a greenhouse, the seedlings were subjected to foliage application with a spray liquid of the wettable powder prepared according to Formulation Example 1. After application, the seedlings were air-dried and then inoculated with MBC-resistant spores of *Pseudocercosporella herpotrichoidas* by spraying a suspension containing the spores. The inoculated seedlings were grown in a dark damp place at 15° C. for 4 days, further incubated for 4 days under illumination, and the controlling effect was examined. The results are shown in Table 7.

TABLE 7

| Compound No. | Concentration of active ingredient (ppm) | Control effect |
|---|---|---|
| present compound | | |
| (3) | 500 | 4 |
| (4) | 500 | 4 |
| (8) | 500 | 4 |
| (9) | 500 | 5 |
| (10) | 500 | 5 |
| (11) | 500 | 5 |
| (12) | 500 | 5 |
| (13) | 500 | 4 |
| (14) | 500 | 5 |
| (15) | 500 | 4 |
| (16) | 500 | 5 |
| (17) | 500 | 5 |
| (18) | 500 | 5 |
| (19) | 500 | 5 |
| (20) | 500 | 5 |
| (21) | 500 | 5 |
| (22) | 500 | 5 |
| (23) | 500 | 5 |
| (25) | 500 | 5 |
| (29) | 500 | 5 |
| (30) | 500 | 4 |
| (32) | 500 | 5 |
| (36) | 500 | 4 |
| (37) | 500 | 5 |
| (39) | 500 | 5 |
| (40) | 500 | 5 |
| (41) | 500 | 5 |
| (42) | 500 | 5 |
| (43) | 500 | 5 |
| (44) | 500 | 5 |
| (46) | 500 | 5 |
| (47) | 500 | 5 |
| (48) | 500 | 5 |
| (49) | 500 | 5 |
| (50) | 500 | 5 |
| (51) | 500 | 4 |
| (52) | 500 | 4 |
| reference compound | | |
| C | 500 | 0 |

TEST EXAMPLE 5

Test for curative controlling effect on speckled leaf blotch (*Septoria tritici*) of wheat Wheat seeds (var.: Norin No. 73) were sown in the sandy loam filled in a plastic pot. After raising for 8 days in a greenhouse, the seedlings were inoculated with spores of *Septoria tritici* by spraying a suspension of spores. The inoculated seedlings were grown in a dark damp place at 15° C. for 3 days, and then grown for 4 days under lightening. The seedlings were subjected to foliage application with a spray liquid of the wettable powder prepared according to Formulation Example 1. After application, the seedlings were grown at 15° C. for 11 days under illumination, and the controlling effect was examined. The results are shown in Table 8.

TABLE 8

| Compound No. | Concentration of active ingredient (ppm) | Control effect |
|---|---|---|
| present compound | | |
| (3) | 500 | 5 |
| (4) | 500 | 5 |
| (5) | 500 | 5 |
| (8) | 500 | 5 |
| (9) | 500 | 5 |
| (10) | 500 | 5 |
| (11) | 500 | 5 |
| (12) | 500 | 5 |
| (13) | 500 | 5 |
| (14) | 500 | 5 |
| (15) | 500 | 5 |
| (16) | 500 | 5 |
| (17) | 500 | 5 |
| (18) | 500 | 5 |
| (19) | 500 | 5 |
| (20) | 500 | 5 |
| (21) | 500 | 5 |
| (22) | 500 | 5 |
| (24) | 500 | 5 |
| (28) | 500 | 5 |
| (29) | 500 | 5 |
| (30) | 500 | 5 |
| (32) | 500 | 5 |
| (36) | 500 | 5 |
| (39) | 500 | 5 |
| (40) | 500 | 5 |
| (41) | 500 | 5 |
| (42) | 500 | 4 |
| (43) | 500 | 5 |
| (46) | 500 | 5 |
| (47) | 500 | 5 |
| (48) | 500 | 5 |
| (49) | 500 | 5 |
| (51) | 500 | 5 |

TABLE 8-continued

| Compound No. | Concentration of active ingredient (ppm) | Control effect |
| --- | --- | --- |
| reference compound | | |
| D | 500 | 0 |

TEST EXAMPLE 6

Test for preventive controlling effect on early leaf spot (*Cercospora arachidicola*) of peanut Peanut seeds (var.: Chiba Handachi) were sown in the sandy loam filled in a plastic pot. After raising for 10 days in a greenhouse, the seedlings, with the second to third foliage leaves open, were subjected to foilage application with a spray liquid of the wettable powder prepared according to Formulation Example 1. After application, the seedlings were air-dried and then inoculated with spores of *Cercospora arachidicola* by spraying a suspension containing the spores. The inoculated seedlings were grown in a damp place at 24° C. for 3 days, and then grown in a constant temperature room for 12 days. The controlling effect was examined. The results are shown in Table 9.

TABLE 9

| Compound No. | Concentration of active ingredient (ppm) | Control effect |
| --- | --- | --- |
| present compound | | |
| (4) | 500 | 5 |
| (9) | 500 | 5 |
| (11) | 500 | 5 |
| (12) | 500 | 5 |
| (13) | 500 | 5 |
| (15) | 500 | 5 |
| (18) | 500 | 5 |
| (23) | 500 | 5 |
| (25) | 500 | 5 |
| (32) | 500 | 5 |
| (33) | 500 | 5 |
| reference compound | | |
| E | 500 | 4 |

We claim:

1. A pyridine derivative represented by the formula,

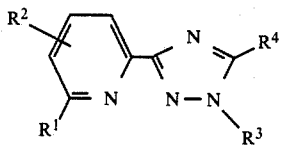

wherein $R^1$ is a $C_1-C_7$ alkyl group; $R^2$ is a hydrogen atom or a $C_1-C_2$ alkyl group; $R^3$ is a $C_1-C_4$ alkyl group; and $R^4$ is a $C_2-C_8$ alkyl group, a $C_3-C_7$ cycloalkyl group, $C_4-C_7$ alkycycloalkyl or a $C_1-C_3$ alkyl group substituted with a $C_3-C_7$ cycloalkyl group.

2. A pyridine derivative according to claim 1, wherein $R^2$ is a hydrogen atom, $R_3$ is a methyl group, and $R^4$ is a $C_3-C_6$ cycloalkyl group, an isopropyl group or a tert-butyl group.

3. 6-Butyl-2-(5-isopropyl-1-methyl-1,2,4-triazole-3-yl)-pryidine.

4. 6-Ethyl-2-(5-cyclohexyl-1-methyl-1,2,4-triazole-3-yl)-pyridine.

5. A fungicidal composition which comprises an effective amount of a pyridine derivative represented by the formula

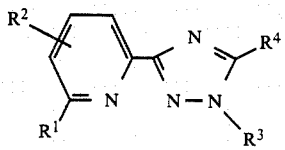

wherein $R^1$ is a $C_1-C_7$ alkyl group; $R^2$ is a hydrogen atom or a $C_1-C_2$ alkyl group; $R^3$ is a $C_1-C_4$ alkyl group; and $R^4$ is a $C_2-C_8$ alkyl group, a $C_3-C_7$ cycloalkyl group, $C_4-C_7$ alkylcycloalkyl, or a $C_1-C_3$ alkyl group substituted with a $C_3-C_7$ cycloalkyl group as an active ingredient, and an inert carrier.

6. A fungicidal composition according to claim 5, wherein $R^2$ is a hydrogen atom, $R^3$ is a methyl group, and $R^4$ is a $C_3-C_6$ cycloalkyl group, an isopropyl group or a tert-butyl group.

7. A method for controlling fungi which comprises applying a fungicidally effective amount of a pyridinyl-pyrimidine derivative represented by the formula,

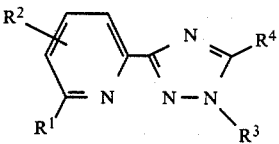

wherein $R^1$ is a $C_1-C_7$ alkyl group; $R^2$ is a hydrogen atom or a $C_1-C_2$ alkyl group; $R^3$ is a $C_1-C_4$ alkyl group; and $R^4$ is a $C_2-C_8$ alkyl group, a $C_3-C_7$ cycloalkyl group, $C_4-C_7$ alkylcycoalky group or a $C_1-C_3$ alkyl group substituted with a $C_3-C_7$ cycloalkyl group, to fungi.

8. A pyridine derivative according to claim 1 wherein $R_4$ is a $C_3-C_7$ cycloalkyl substituted by methyl.

9. A fungicidal composition according to claim 5 wherein $R_4$ is $C_3-C_7$ cycloalkyl substituted by methyl.

10. The process of claim 7 wherein $R_4$ is $C_3-C_7$ cycloalkyl substituted by methyl.

* * * * *